US00PP22897P3

(12) United States Plant Patent
Meilland

(10) Patent No.: US PP22,897 P3
(45) Date of Patent: Jul. 31, 2012

(54) HYBRID TEA ROSE PLANT NAMED 'MEIGRILEGA'

(50) Latin Name: *Rosa hybrida*
Varietal Denomination: Meigrilega

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/923,706

(22) Filed: Oct. 5, 2010

(65) Prior Publication Data

US 2012/0084891 P1 Apr. 5, 2012

(51) Int. Cl.
*A01H 5/00* (2006.01)

(52) U.S. Cl. ..... Plt./130

(58) Field of Classification Search ..... Plt./130, Plt./131, 138
See application file for complete search history.

*Primary Examiner* — June Hwu
(74) *Attorney, Agent, or Firm* — Buchanan Ingersoll & Rooney PC

(57) ABSTRACT

A new and distinct Hybrid Tea rose plant is provided that abundantly and substantially continuously forms attractive fully double magenta blossoms that are lavender-pink on the reverse. The blossom configuration is somewhat formal and displays well when cut and placed in a vase. The plant exhibits vigorous vegetation and an upright and bushy growth habit. The foliage is ornamental dark green with a glossy finish. A sweet fragrance is provided by the blossoms. The plant is well suited for growing as attractive ornamentation in parks and gardens.

1 Drawing Sheet

Botanical/commerical classification: *Rosa hybrida*/Hybrid Tea Rose Plant.

Varietal denomination: cv. Meigrilega.

SUMMARY OF THE INVENTION

The new variety of *Rosa hybrida* Hybrid Tea rose plant of the present invention was created in France by artificial pollination during June 1998 wherein two parents were crossed which previously had been studied in the hope that they would contribute the desired characteristics. The female parent (i.e., the seed parent) was the 'Meigriso' variety (non-patented in the United States). The male parent (i.e., the pollen parent) of the new variety was the 'Twobe' variety (U.S. Plant Pat. No. 7,901). The parentage of the new variety can be summarized as follows:

'Meigriso'×'Twobe'.

The seeds resulting from the above pollination were sown and small plants were obtained which were physically and biologically different from each other. Selective study resulted in the identification of a single plant of the new variety.

It was found that the new Hybrid Tea rose plant of the present invention possesses the following combination of characteristics:

(a) abundantly and substantially continuously forms attractive fully double magenta blossoms that are lavender-pink on the reverse,
(b) exhibits an upright and bushy growth habit,
(c) forms vigorous vegetation,
(d) forms attractive ornamental dark green foliage with a glossy finish, and
(e) is well suited for providing attractive ornamentation in the landscape.

The new variety well meets the needs of the horticultural industry. It can be grown to advantage as ornamentation in parks, gardens, public areas, and in residential settings. The new variety is particularly well suited for providing attractive ornamentation in the landscape. During observations to date the disease resistance has been above average for the type. The brightly colored magenta blossoms contrast nicely with the ornamental dark green foliage. Additionally, the blossom configuration is somewhat formal and displays well when cut and placed in a vase.

The new variety of the present invention can be readily distinguished from its ancestors through an inspection of the blossom coloration. More specifically, the 'Meigriso' variety forms ruby-red blossoms that are whitish on the reverse, and the 'Twobe' variety forms blossoms that are Neyron Rose to Rhodonite Red in coloration.

The new variety of the present invention also can be readily distinguished from other fragrant Hybrid Tea rose varieties such as the 'Wezeip' variety (U.S. Plant Pat. No. 4,552) and the 'Tanallepal' variety (non-patented in the United States). More specifically, the blossoms of the 'Wezeip' variety display a lesser number of petals and are of a dissimilar silvery lavender coloration shading to ruby-red at the edges. The blossoms of the 'Tanallepal' variety also display a lesser number of petals and are of a dissimilar color combination wherein the upper surface is cherry red and the under surface is white-to-silver.

The characteristics of the new variety have been found at Le Cannet-des-Maures, Var, France, and at Waso, Calif., U.S.A., to be homogeneous and stable and to be strictly transmissible by asexual propagation, such as budding, grafting, and the rooting of cuttings from one generation to another. Accordingly, the new variety reproduces in a true-to-type manner by such asexual propagation.

The new variety has been named 'Meigrilega' and will be marketed in the United States under the GIRLS' NIGHT OUT trademark.

BRIEF DESCRIPTION OF THE PHOTOGRAPH

The accompanying photograph shows, as nearly true as it is reasonably possible to make the same in a color illustration of this character, a representative blossom and foliage of the new variety.

The plant was approximately two years of age and was observed during June while growing outdoors in a container at West Grove, Pa., U.S.A.

DETAILED DESCRIPTION

The chart used in the identification of colors is that of The Royal Horticultural Society (R.H.S. Colour Chart—1995 or equivalent), London, England. The description is based on the observation of two-year-old specimens of the new variety during June while growing outdoors in containers at West Grove, Pa., U.S.A.

Class: Hybrid Tea.

Plant:

*Height.*—Approximately 1.6 m on average at the end of the growing season.

*Width.*—Approximately 1 m on average at the end of one growing season.

*Habit.*—Upright and bushy.

Branches:

*Color.*—Young stems: near Yellow-Green Group 144B. Adult wood: Yellow-Green Group 146B.

*Thorns.*—Size: approximately 5 mm in length, approximately 4 mm in width at the base, and commonly near Greyed-Red Group 178A in coloration when immature, and commonly near Greyed-Red Group 184A when fully mature.

*Texture.*—Young stems: smooth with short hairs. Adult wood: Smooth with occasional rough patches.

Leaves:

*Size.*—A five-leaflet leaf commonly is approximately 11.6 cm in length on average and approximately 8.9 cm on average at the widest point. Number: 3, 5 and 7. Length: approximately 7 cm on average for a terminal leaflet, and approximately 4.5 cm on average for a lower leaflet. Width: approximately 5 cm on average at the widest point for a terminal leaflet, and approximately 3 cm on average at the widest point for a lower leaflet. Shape: ovate with a rounded base and a somewhat acuminate tip. Margins: denticulate. Texture: smooth on both surfaces, and with a coarse midrib on the under surface. Overall appearance: ornamental, attractive dark green with a glossy upper surface. Color (young foliage): Upper surface: commonly Yellow-Green Group 147A. Under surface: commonly Yellow-Green Group 146B and substantially suffused with Greyed-Purple Group 184B. Color (adult foliage): Upper surface: commonly near Yellow-Green Group 147A. Under surface: commonly near Yellow-Green Group 147B.

Inflorescence:

Number of flowers.—Commonly up to approximately 10 blooms on a plant at a given time.

*Petioles.* —Length: commonly approximately 3 cm on average. Diameter: approximately 1 mm on average. Texture: smooth and covered with short hairs. Color: on the upper surface near Yellow-Green Group 146C overlaid with Greyed-Orange Group 166A.

*Stipules.*—Length: approximately 1.5 cm on average. Width: approximately 5 mm on average. Texture: smooth on the upper surface and with short hairs on the under surface. Color: near Yellow-Green Group 146C.

*Peduncle.*—Near Yellow-Green Group 144A in coloration, smooth in texture with short hairs, commonly approximately 7.5 mm in length on average, and approximately 7 mm in diameter on average.

*Sepals.*—Upper surface: smooth, slightly fuzzy in texture, hirsute, and commonly near Yellow-Green Group 145A in coloration with darker coloration of Green Group 138A towards the margins. Under surface: smooth, and near Yellow-Green Group 144A in coloration. Size: commonly approximately 4.5 cm in length on average, and approximately 1 cm in width at the base. Number: five.

*Buds.*—Shape: generally ovoid. Length: approximately 3 cm on average as the calyx breaks. Diameter: approximately 1.2 cm on average as the calyx breaks. Color: Red Group 71C.

*Flower.*—Form: somewhat formal, and fully double. Diameter: approximately 14 cm on average when fully open. Color (when opening begins): upper surface: near Red-Purple Group 57B highlighted with Red-Purple Group 60A at the petal edges. under surface: near Red-Purple Group 64D. Color (at end of blooming): upper surface: near Red Group 55B suffused with Red Group 55A at the petal edges. under surface: near Red Group 56A. Fragrance: sweet scent. Petal number: commonly approximately 43 to 45 on average. Petal size: commonly approximately 3.5 cm on average in length, and approximately 3.7 cm on average in width. Petal shape: generally obovate. Petal texture: generally smooth. Petal apex: obtuse. Petal base: rounded. Petaloids: absent during observations to date. Petal drop: the petals commonly drop cleanly at full maturity. Stamen: approximately 115 to 120 on average, and regularly arranged about the pistils. Anthers: commonly approximately 3 mm in length, approximately 2 mm in width, and near Yellow Group 11A in coloration. Filaments: approximately 5 mm in length on average, and near Orange-Red Group 33A in coloration. Pistils: approximately 140 to 145 on average, and separate and free. Styles: commonly approximately 5 to 8 mm in length, and near Greyed-Orange Group 164A in coloration. Stigmas: approximately 1 mm in diameter, and near Red-Purple Group 61D in coloration. Receptacle: achenes stand on the bottom and wall, generally round in shape, smooth in texture, commonly approximately 7 mm in length, and approximately 8 mm in width, and near Green Group 143C in color.

Development:

*Vegetation.*—Vigorous and strong.

*Blossoming.*—Abundant and substantially continuous during the growing season.

*Resistance to disease.*—Above average for Blackspot, Mildew, and Rust during observations to date.

*Formation of hips/seeds.*—None have been observed during observations to date.

I claim:

1. A new and distinct Hybrid Tea rose plant characterized by the following combination of characteristics:

(a) abundantly and substantially continuously forms attractive fully double magenta blossoms that are lavender-pink on the reverse, (b) exhibits an upright and bushy growth habit, (c) forms vigorous vegetation, (d) forms attractive ornamental dark green foliage with a glossy finish, and (f) is well suited for providing attractive ornamentation in the landscape; substantially as herein shown and described.

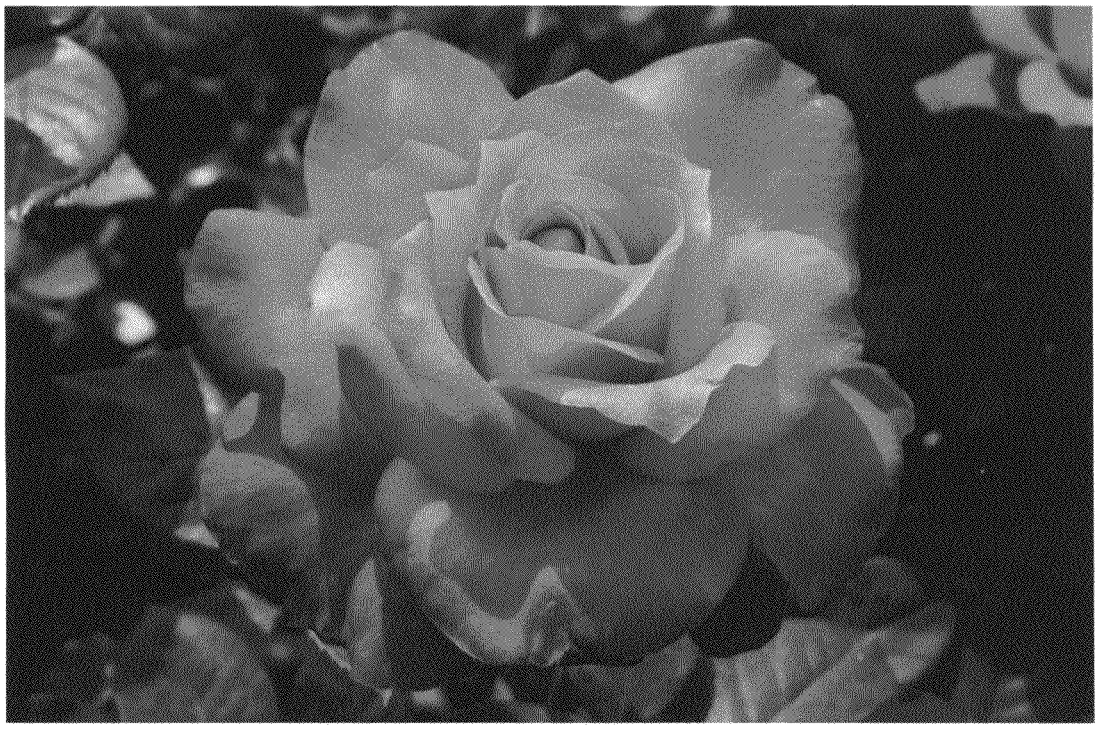

* * * * *